(12) United States Patent
Beckman et al.

(10) Patent No.: US 10,213,893 B2
(45) Date of Patent: Feb. 26, 2019

(54) INTEGRAL PART WEAR INDICATOR SYSTEM, METHOD AND APPARATUS

(71) Applicant: United Technologies Corporation, Hartford, CT (US)

(72) Inventors: Micah Beckman, Middletown, CT (US); Daniel Livchitz, West Hartford, CT (US); Edward Marchitto, Canton, CT (US); David Masiukiewicz, Vernon, CT (US)

(73) Assignee: United Technologies Corporation, Farmington, CT (US)

( * ) Notice: Subject to any disclaimer, the term of this patent is extended or adjusted under 35 U.S.C. 154(b) by 444 days.

(21) Appl. No.: 15/076,807

(22) Filed: Mar. 22, 2016

(65) Prior Publication Data

US 2016/0201502 A1  Jul. 14, 2016

Related U.S. Application Data

(63) Continuation of application No. PCT/US2014/068196, filed on Dec. 2, 2014.

(60) Provisional application No. 61/915,887, filed on Dec. 13, 2013.

(51) Int. Cl.

| | |
|---|---|
| *B24B 19/14* | (2006.01) |
| *F01D 9/04* | (2006.01) |
| *F04D 29/54* | (2006.01) |
| *G01N 3/56* | (2006.01) |
| *B24C 1/08* | (2006.01) |
| *F01D 5/00* | (2006.01) |
| *F01D 21/00* | (2006.01) |
| *B24C 3/32* | (2006.01) |

(52) U.S. Cl.
CPC ............ *B24B 19/14* (2013.01); *B24C 1/08* (2013.01); *B24C 3/327* (2013.01); *F01D 5/005* (2013.01); *F01D 9/041* (2013.01); *F01D 21/003* (2013.01); *F04D 29/542* (2013.01); *G01N 3/56* (2013.01); *F05D 2230/10* (2013.01)

(58) Field of Classification Search
CPC ..................................................... B24B 19/14
USPC ............................................................ 73/7
See application file for complete search history.

(56) References Cited

U.S. PATENT DOCUMENTS

| | | | |
|---|---|---|---|
| 6,394,023 B1 | 5/2002 | Crocker | |
| 8,695,445 B2 * | 4/2014 | Laurer | F01D 5/12 116/208 |
| 8,919,202 B2 * | 12/2014 | Keely | F01D 17/02 702/35 |

(Continued)

FOREIGN PATENT DOCUMENTS

WO    2013088078    6/2013

OTHER PUBLICATIONS

International Preliminary Report on Patentability dated Jun. 14, 2016 in Application No. PCT/US2014/068196.

(Continued)

*Primary Examiner* — John Fitzgerald
*Assistant Examiner* — Rodney T Frank
(74) *Attorney, Agent, or Firm* — Snell & Wilmer L.L.P.

(57) ABSTRACT

A part comprising a one or more removable wear indicators is provided. The part may be a stator segment comprising a plurality of airfoils. The stator segment may also comprise one or more mock airfoils at each end of the stator segment. Each of the mock airfoils may comprise an indicator configured to wear during a polishing process.

8 Claims, 6 Drawing Sheets

(56) References Cited

U.S. PATENT DOCUMENTS

| | | | |
|---|---|---|---|
| 9,315,663 B2* | 4/2016 | Appleby | C08L 63/00 |
| 9,764,447 B2* | 9/2017 | Beckman | B24B 19/14 |
| 2003/0027495 A1 | 2/2003 | Shaw | |
| 2009/0173418 A1 | 7/2009 | Jayabalan | |
| 2009/0282677 A1* | 11/2009 | Korn | B23P 6/007 |
| | | | 29/889.1 |
| 2011/0047777 A1 | 3/2011 | Soucy et al. | |
| 2011/0116906 A1 | 5/2011 | Smith et al. | |
| 2012/0285226 A1 | 11/2012 | Laurer et al. | |
| 2013/0112366 A1 | 5/2013 | Mottin et al. | |

OTHER PUBLICATIONS

International Search Report and Written Opinion dated Apr. 14, 2015 in Application No. PCT/US2014/068196.

* cited by examiner

INTEGRAL PART WEAR INDICATOR SYSTEM, METHOD AND APPARATUS

CROSS-REFERENCE TO RELATED APPLICATIONS

This application is a continuation of, claims priority to and the benefit of, PCT/US2014/068196 filed on Dec. 2, 2014 and entitled "INTEGRAL PART WEAR INDICATOR SYSTEM, METHOD AND APPARATUS," which claims priority from U.S. Provisional Application No. 61/915,887 filed on Dec. 13, 2013 and entitled "INTEGRAL PART WEAR INDICATOR SYSTEM, METHOD AND APPARATUS." Both of the aforementioned applications are incorporated herein by reference in their entirety.

FIELD

The present disclosure relates to part wear indicators, and more specifically, integrally formed part wear indicators for parts subject to abrasive processing.

BACKGROUND

Aerospace parts such as stators and other precisely manufactured devices may require specialized finishing processes, including, for example, abrasive finishing, precision grinding, super polishing and/or the like. These processes may involve immersion or contact with abrasive materials. Monitoring part wear may improve manufacturing efficiency and lower part production costs.

SUMMARY

In various embodiments, a stator segment may comprise a plurality of airfoils, a first mock airfoil and a second mock airfoil. The first mock airfoil may be formed on a first end of the stator. The second mock airfoil may be formed on a second end of the stator. The first mock airfoil and the second mock airfoil may be removed in response to the completion of a polishing process.

A part wear monitoring system comprising a stator segment is provided. In various embodiments, the stator segment may comprise a first plurality of integrally formed airfoils, a first integrally formed inspection surface and a second integrally formed inspection surface. The first integrally formed inspection surface may comprise a first wear indicator. The second integrally formed inspection surface may comprise a second wear indicator.

In various embodiments, an abrasive process monitoring system may comprise a part, a first inspection feature and a second inspection feature. The party may comprise a plurality of integrally formed features. The first inspection feature may comprise a first wear indicator. The first inspection feature may be formed adjacent to at least one of the integrally formed features. The second inspection feature may comprise a second wear indicator. The second inspection feature may be formed adjacent to at least one of the integrally formed features. At least one of the first inspection feature and the second inspection feature may be removed in response to a level of wear showing on at least one of the first wear indicator and the second wear indicator.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may be obtained by referring to the detailed description and claims when considered in connection with the drawing figures, wherein like numerals denote like elements.

DETAILED DESCRIPTION

The detailed description of exemplary embodiments herein makes reference to the accompanying drawings, which show exemplary embodiments by way of illustration. While these exemplary embodiments are described in sufficient detail to enable those skilled in the art to practice the inventions, it should be understood that other embodiments may be realized and that logical, chemical and mechanical changes may be made without departing from the spirit and scope of the disclosure. Thus, the detailed description herein is presented for purposes of illustration only and not of limitation. For example, the steps recited in any of the method or process descriptions may be executed in any order and are not necessarily limited to the order presented.

Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

As used herein, phrases such as "make contact with," "coupled to," "touch," "interface with" and "engage" may be used interchangeably. Different surface shading may be used throughout the figures to denote different parts but not necessarily to denote the same or different materials.

Figure 1:
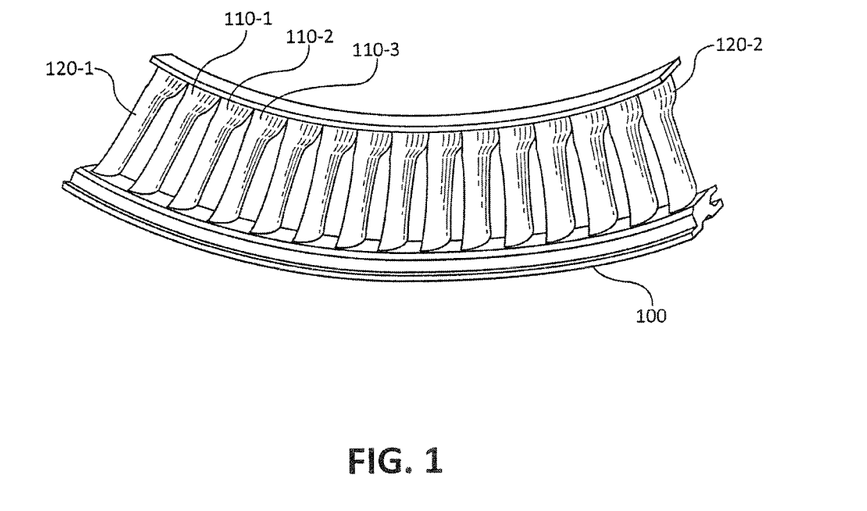
FIG. 1 illustrates a front perspective view of a stator segment, in accordance with various embodiments.

In various embodiments, and with reference to FIG. 1, a stator segment 100 (e.g., or other part) may comprise one or more airfoils 110 and/or features (e.g., three shown as airfoil 110-1, airfoil 110-2, and airfoil 110-3, etc. in FIG. 1). Stator segment 100 may be manufactured using direct metal laser sintering ("DMLS"). DMLS may comprise fusing metal powder into a solid part by melting it locally using a laser.

In various embodiments, the DMLS process allows a manufacturer of stator segment 100 to create stator segments 100 of any suitable size, shape, and/or geometry. Moreover, the DMLS process allows a manufacturer to create features on stator segment 100 that may be used for manufacturing, inspection, wear detection, quality control, and/or the like. For example, stator segment 100 may comprise one or more mock airfoils 120 and/or a wear indicating feature (shown as mock airfoil 120-1 and mock airfoil 120-2 in FIG. 1). Mock airfoils 120 may comprise wear indicators, reference locations, and/or the like.

Figure 2:
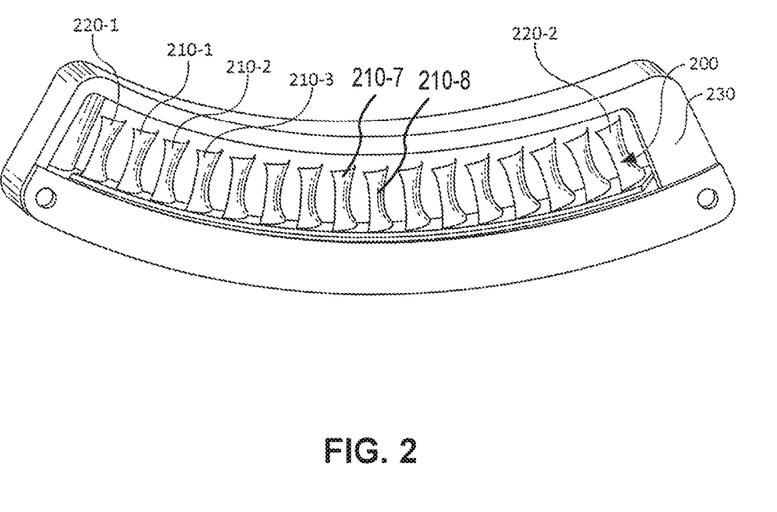
FIG. 2 illustrates a front perspective view of a stator segment installed within a tool, in accordance with various embodiments.

In various embodiments and with reference to FIG. 2, stator segment 200 may be installed in a suitable tool 230 for further processing. For example, after DMLS processing, stator segment 200 may be relatively rough. Stator segment 200 may be subjected to abrasive processing and/or polishing to improve overall stator and/or airfoil 210 performance.

In various embodiments, airfoils 210 and mock airfoils 220 have been dimensionally pretargeted to compensate for abrasive wear during the polishing processes. The polishing process for DMLS stators may include, for example, grit blast, abrasive flow machining and/or super polishing.

In various embodiments, inner airfoils 210 (e.g., airfoil 210-7 and/or airfoil 210-8) may experience greater abrasive wear than outer airfoils 210 (e.g., airfoil 210-1 and/or airfoil 210-2 and/or airfoil 210-3) during the polishing process. This may be due to the abrasive flow media behaving as a fluid. The media may have reduced fluid velocity at its boundaries (e.g., at the cavity walls of the abrasive flow machining cavity). Thus, the airfoils 210 on the ends (e.g., airfoil 210-1 and/or airfoil 210-2 and/or airfoil 210-3) of stator segment 200 experience less wear than the airfoils 210 towards the middle of stator segment 200 (e.g., airfoil 210-7 and/or airfoil 210-8). To reduce the variation in wear, mock airfoils may be added to the end of stator segment 200 (e.g., 220-1 and 220-2). Mock airfoils 220 may be used to monitor the wear on stator segment 200 throughout the polishing process. Thereafter, mock airfoils 220 may be removed and/or cut-off of stator segment 200 and discarded.

Figure 3A:
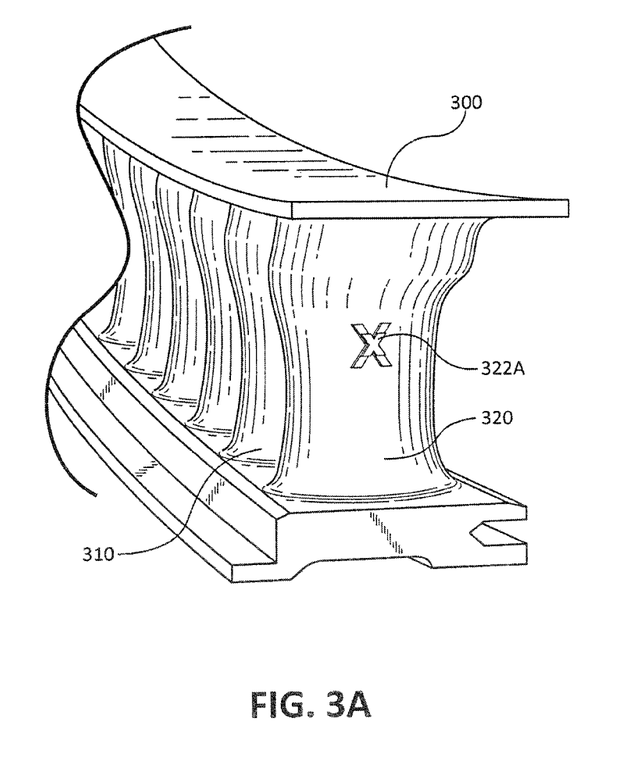
FIG. 3A illustrates a side perspective view of a portion of stator segment comprising a mock airfoil including a first wear indicator, in accordance with various embodiments.
Figure 3B:
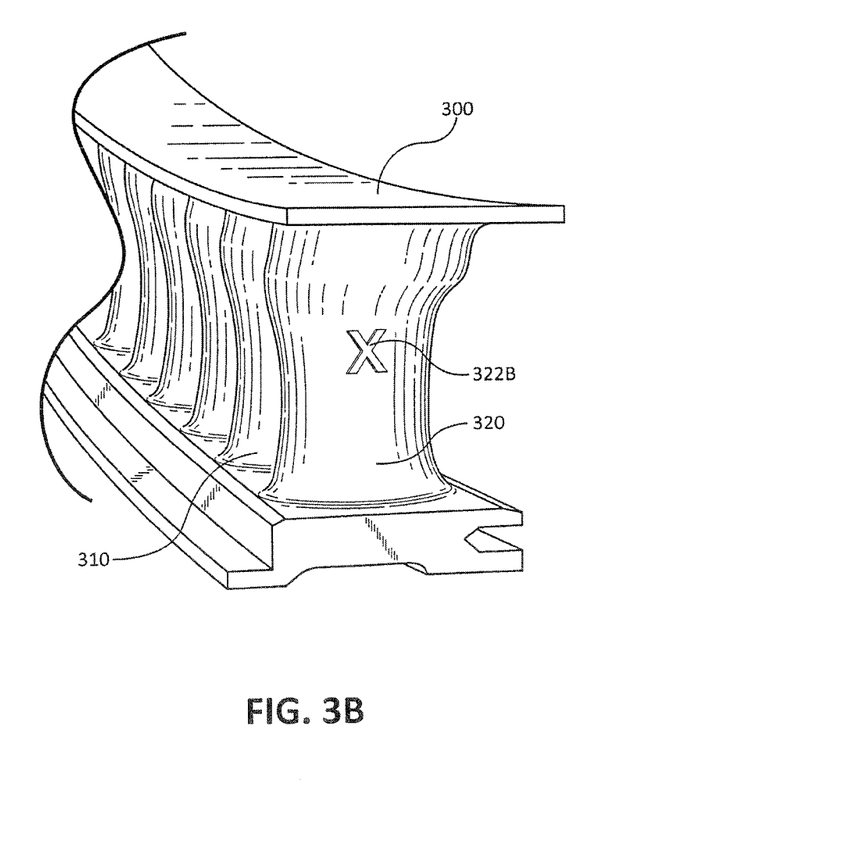
FIG. 3B illustrates a side perspective view of a portion of stator segment comprising a mock airfoil including a second wear indicator, in accordance with various embodiments.
Figure 3C:
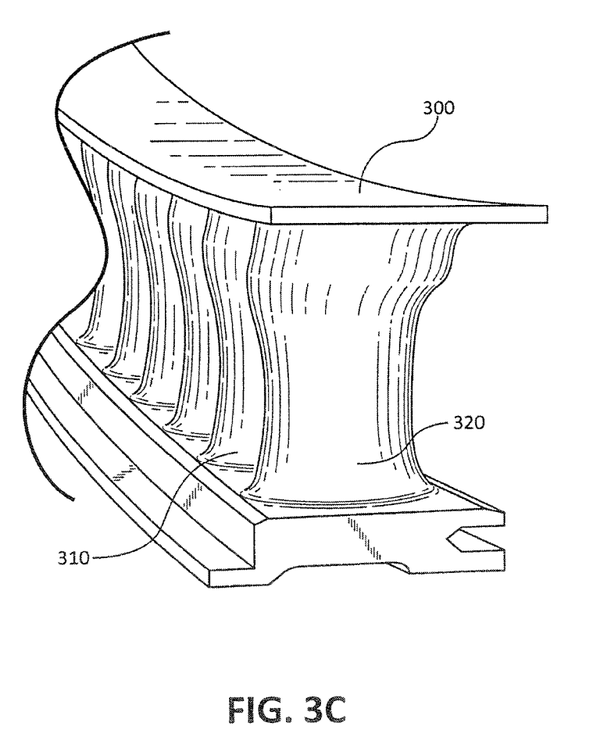
FIG. 3C illustrates a side perspective view of a portion of stator segment comprising a mock airfoil, in accordance with various embodiments.

In various embodiments and with reference to FIGS. 3A-3C, wear on stator segment 300 may be evaluated by observing a wear indicator 322 integrally formed on mock airfoil 320 disposed proximal inner airfoils 310. Wear indicator 322 may be configured to function as a rapid, efficient, visual inspection system for stator segment 300. For example, wear indicator 322 may be inspected before and after various steps of the polishing process to determine whether a particular polishing process has removed too much material or too little material from stator segment 300.

In various embodiments, stator segment 300 may be abrasively processed by, for example, abrasive flow machining ("AFM"). After AFM, and prior to an inspection and/or quality control step, stator segment 300 may be further processed by super polishing or another suitable process. To determine whether AFM was successful and prior to super polishing, wear indicator 322 may be visually and/or physically (e.g., touched) inspected. Wear indicator 322 may be configured to wear a predetermined amount during AFM. If wear indicator 322 exhibits excessive wear, stator segment 300 may be scraped. This may eliminate the cost of further processing a part that will not be suitable for commercial use.

In various embodiments, wear indicator 322 may be initially created on mock airfoil 320 as wear indicator 322A as shown in FIG. 3A. Wear indicator 322 may be a single surface or a plurality of surfaces. For example, where wear indicator 322 is a single surface, wear indicator 322 may be shaped as a dome. Wear indicator 322A may have a first raised surface and a second raised surface disposed at least partially on the first raised surface. In this regard, the predetermined wear portion may wear or be eroded from wear indicator 322A during the AFM process. In response to the AFM process being complete, stator segment 300 may be inspected and/or visually evaluated. More specifically, mock airfoil 320 and wear indicator 322 may be evaluated to determine whether the AFM process was successful. Wear indicator 322 may be inspected to determine whether wear indicator 322 is sufficiently visible and/or tall. In this regard, wear indicator 322 may be wear indicator 322B after the second raised surface has worn away as shown in FIG. 3B, indicating that the AFM process was successful. Where no wear indicator 322 is visible on mock airfoil 320, as shown in FIG. 3C, stator segment 300 may have been worn excessively during the AFM process. As a result, stator segment 300 may be scrapped before further processing. This intermediate or preliminary inspection may provide savings and/or increase manufacturing efficiency.

Figure 4A:
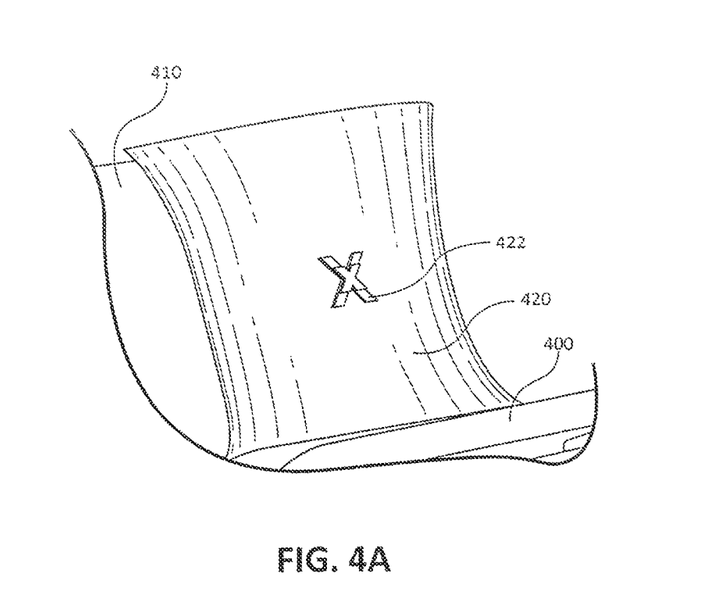
FIGS. 4A-4B illustrate a view of a mock airfoil comprising a wear indicator, in accordance with various embodiments.
Figure 4B:
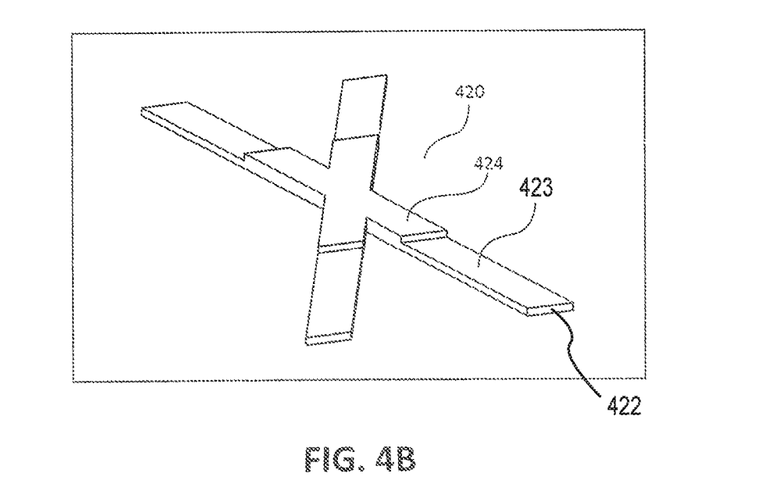

In various embodiments and with reference to FIGS. 4A-4B, wear indicator 422 may be formed on mock airfoil 420 of stator segment 400 comprising airfoils 410. Wear indicator 422 may comprise a first surface 423 and a second surface 424. First surface 423 and second surface 424 may be stacked on one another. Moreover, first surface 423 and second surface 424 may be configured in a stacked "X" shape. While first surface 423 and second surface 424 may be any suitable shape, first surface 423 and second surface 424 may be a shape that engages both axial and radial flow so that wear during the abrasive flow machining and/or polishing processes can be accurately estimated.

In various embodiments and with reference to FIG. 1, mock airfoil 120 may be removable during one or more machining steps after abrasive flow machining and/or completion of the polishing process of stator segment 100. In this regard, mock airfoil 120 may be included to evaluate wear, control quality, and/or aid in manufacturing of stator segment 100. Mock airfoils 120 may then be removed and discarded once the polishing process is complete.

In various embodiments, the systems and methods described herein may be discussed in the context of stator segments and/or abrasive processing of stator structures. However, the systems and methods described herein may be used with any suitable part and/or party processing that includes wear inducing operations and/or processing. Moreover, the systems and methods described herein may be used with cast parts, machined parts and/or any other suitable parts that are subjecting to wear inducing operations and/or processing.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions. The scope of the inventions is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment", "an embodiment", "various embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

What is claimed is:

1. A part wear monitoring system, comprising:
a stator segment, comprising:
a plurality of integrally formed airfoils; and
a mock airfoil disposed proximal the plurality of integrally formed airfoils:
wherein the mock airfoil comprises a wear indicator configured to engage axial and radial flow of a fluid during at least one of an abrasive machining process and a polishing process, and the mock airfoil is configured to be removed after at least one of the abrasive machining process and the polishing process.

2. The part wear monitoring system of claim 1, wherein the wear indicator comprises a first raised surface and a second raised surface that is thicker than the first raised surface.

3. The part wear monitoring system of claim 2, wherein the second raised surface is disposed on the first raised surface.

4. The part wear monitoring system of claim 1, wherein the wear indicator comprises an "X" shape.

5. The part wear monitoring system of claim 2, wherein the first raised surface and the second raised surface are integrally formed.

6. The part wear monitoring system of claim 1, wherein the mock airfoil is removed in response to completion of at least one of the abrasive machining process and the polishing process.

7. The part wear monitoring system of claim 2, wherein the second raised surface is thicker than the first raised surface in an axial direction of the stator segment.

8. The part wear monitoring system of claim 1, wherein the mock airfoil is subject to greater wear from at least one of the abrasive machining process and the polishing process than the integrally formed airfoils.

* * * * *